US006875618B2

(12) United States Patent
Bandura et al.

(10) Patent No.: US 6,875,618 B2
(45) Date of Patent: Apr. 5, 2005

(54) METHOD FOR PHOSPHORUS QUANTITATION

(75) Inventors: Dmitry R. Bandura, Aurora (CA); Vladimir I. Baranov, Richmond Hill (CA); Scott D. Tanner, Aurora (CA)

(73) Assignee: MDS Inc., Concord (CA)

( * ) Notice: Subject to any disclaimer, the term of this patent is extended or adjusted under 35 U.S.C. 154(b) by 211 days.

(21) Appl. No.: 10/198,099

(22) Filed: Jul. 19, 2002

(65) Prior Publication Data

US 2003/0044994 A1 Mar. 6, 2003

Related U.S. Application Data

(60) Provisional application No. 60/306,152, filed on Jul. 19, 2001.

(51) Int. Cl.[7] .............................................. G01N 33/00
(52) U.S. Cl. ..................... 436/104; 436/103; 436/173; 436/86
(58) Field of Search ......................... 436/173, 86, 103, 436/104

(56) References Cited

U.S. PATENT DOCUMENTS 6,140,638 A   10/2000   Tanner et al. ............... 250/282

OTHER PUBLICATIONS

Wind et al. "Analysis of Protein Phosphorylation by Capillary Liquid Chromatography Coupled to Element Mass Spectrometry with 31P Detection and to Electrospray Mass Spectrometry", Analytical Chemistry (2001), 73(1), 29–35.*

Resing et al. (1995) Mass Spectrometric Analysis of 21 Phosphorylation Sites in the Internal Repeat of Rat Profilaggrin, Precursor of an Intermediate Filament Associated Protein, *Biochemistry* 34: 9477–9487.

Tanner et al. (1999) A Dynamic Reaction Cell for Inductively Coupled Plasma Mass Spectrometry (ICPDRC–MS). II. Reduction of Interferences Produced Within the Cell, *J. Am. Soc. Mass Spectrom.* 10: 1083–1094.

Wind et al. (2001) Protein Phosphorylation Degree: Determination by Capillary Liquid Chromotography and Inductively Coupled Plasma Mass Spectrometry, *Anal. Chem.* 73: 3006–3010.

* cited by examiner

*Primary Examiner*—Yelena G. Gakh
(74) *Attorney, Agent, or Firm*—Morgan, Lewis & Bockius LLP

(57) ABSTRACT

A method of detecting and measuring phosphorus in samples is disclosed. The measurement of phosphorylation is made with an inductively coupled plasma mass spectrometer (ICP-MS), coupled to a reactive collision cell. The reactive collision cell is employed to ensure interference-free detection of phosphorus ions, by the formation of product ions with a different mass to charge ratio. Accurate measurement of phosphorylation in samples is important in proteomics.

17 Claims, 8 Drawing Sheets

METHOD FOR PHOSPHORUS QUANTITATION

This application claims the benefit of provisional application No. 60/306,152, filed Jul. 19, 2001.

FIELD OF THE INVENTION

The invention relates to the detection and measurement of the degree of phosphorylation in samples, particularly biological samples. The present invention relates to the field molecular biology and proteomics, coupled to the field of analytical chemistry.

BACKGROUND OF THE INVENTION

Organisms have evolved mechanisms to control cellular processes by the addition and removal of phosphate groups to and from molecules. Organisms use phosphorylation and dephosphorylation to transmit and integrate signals from their environment. For example, a pollen grain landing on a stigma leads to a series of protein phosphorylation events that ultimately triggers the onset of fertilization. In addition, phosphorylation is a mechanism for cellular regulation of processes such as cell division, cell growth and cell differentiation. In proteins, a phosphate group can modify serine, threonine, tyrosine, histidine, arginine, lysine, cysteine, glutamic acid and aspartic acid residues.

The emerging field of proteomics deals with the characterization and regulation of proteins in organisms. Since phosphorylation plays such a major role in protein regulation, there is a need for an accurate, fast, simple and inexpensive method to measure the degree of phosphorylation in samples.

Currently, the methods used to detect phosphorylation in a sample include fluorescent assays, radioimmunoassays, immobilized metal affinity chromatography (IMAC), two-dimensional electrophoretic gel separation (2-D PAGE) coupled with mass spectrometry detection, and liquid chromatography separation coupled with mass spectrometry detection. Normally detection of the mass spectrometer requires electrospray ionization (ESI) or matrix-assisted laser desorption ionization (MALDI). Methods for quantitation of phosphate include $^{31}P$ nuclear magnetic resonance spectroscopy (NMR) and radioisotope ($\gamma$-$^{32}P$) labelling with scintillation counting or multiphoton (MPD) detection (Godovac-Zimmerman and Brown, 2001).

However, the above methods are either laborious or hindered by the need to use radioisotopes, and are not considered quantitative in that they do not precisely determine the number of phosphate groups in the sample. These methods require a two-step process, whereby a portion of the sample is used to determine the phosphorous concentration, and another portion of the sample is used to determine the concentration of the sample. Thus, there is variability in the degree of sample utilization. For example, if one is assaying a protein sample, quantitation of the protein is required to accurately assess the number of phosphorylation sites per protein molecule. This measurement requires a completely different assay done independently of phosphate detection. The only truly accurate method for determining protein concentration is to acid hydrolyse a portion of the sample and then perform amino acid analysis on the hydrolysate (Wilson and Walker, 2000). Other approximate methods rely on the presence of particular amino acid residues in the proteins. For example, tyrosine and tryptophan are measured in ultraviolet absorption, and arginine and lysine are measured in the Bradford™ calorimetric assay. The Kjeldahl analysis measures total nitrogen, and the far ultraviolet absorption method is based on the number of peptide bonds. However, these assays are relative as the concentration of particular amino acid residues and even nitrogen in proteins varies significantly (Wilson and Walker, 2000).

Recently, Wind et al. (2001) disclosed a method for determining the degree of protein phosphorylation by the simultaneous detection of phosphorus and sulfur ions using inductively coupled plasma mass spectrometry (ICP-MS). However, this method required 'adjustments' to avoid or minimize isobaric interference. For example, a very slow flow rate was required (4 microlitre/minute) to minimize isobaric interferences from solvent molecules. The method required the use of 'high resolution' ICP-MS, which is a very expensive instrument and generally is not used for routine measurements. These restrictions make the method laborious and expensive.

Thus, the current methods to determine the degree of phosphorylation of a sample either (i) lack accurate quantitation, (ii) require a two-step process, or (iii) they require a very expensive machine.

The use of ICP-MS to detect phosphorus and quantify the degree of phosphorylation in samples is hindered by the low degree of ionization of phosphorus (33%) and the elements that can characterize a biological sample namely O, N, H (0.1%), C (5%), S (14%). The degrees of ionization given here in the brackets are taken from Houk, R. S., 1986. Another limitation is the presence of high background of these ions that originate from the plasma ion source, sample matrix or the vacuum system of the instrument, and also the presence of spectral interferences of other atomic or polyatomic ions at the same mass of the ions of interest. For example, $^{31}P^+$ is interfered by the presence of $^{15}N\ ^{16}O^+$, $^{14}N^{17}O^+$, $^{14}N^{16}OH^+$ and others. The latter limitation is referred to as isobaric interference.

U.S. Pat. No. 6,140,638 to Tanner and Baranov, discloses a reactive collision cell used in conjunction with an inductively coupled plasma mass spectrometer (ICP-MS), to reduce isobaric interference, by reactive removal of the interference, in which a dynamic bandpass is employed to reject intermediate ions which would otherwise react to form new isobaric interferences. Recently, this reactive collision cell has also been used to produce secondary ions or product ions with a different mass to charge ratio than the interfering ions, to minimize isobaric interference (Baranov and Tanner, 1998; Tanner and Baranov, 1998; Baranov and Tanner, 1999; Tanner and Baranov, 1999; Bollinger and Schleisman, 1999).

WO 01/01446 to Todd et al., 2000 discloses a similar approach to minimize isobaric interference using a different apparatus. Similarly, Eiden et al., 1997, discloses the use of an Ion Trap Mass Spectrometer coupled to an octopole ion guide/collision cell to avoid isobaric interference, by using reactions to remove interferences to a different mass. Both these references use different instruments and do not deal with the detection and measurement of the degree of phosphorylation in samples.

With the great potential offered by the emerging field of proteomics, there is a need for the detection and measurement of the degree of phosphorylation in biological samples. There is a need for rapid method for quantitation, employing simultaneous measurement of the concentration of phosphorus and the concentration of the sample. Further, there is a need for a rapid and accurate confirmation of the results. Further still, there is a need for a simple and cheap method, requiring a small and relatively inexpensive machine.

SUMMARY OF THE INVENTION

The last two decades have seen the improvement of elemental analysis due to the development of the inductively coupled plasma (ICP) source using mass or optical spectrometry. This has resulted in ultra sensitive spectrometers with high matrix tolerance and means of resolving isotopic and spectral interferences. The present invention has coupled the developments in this field with the continuing need to provide rapid and precise detection and measurement in biological assays.

The invention discloses a method to determine the degree of phosphorylation in a sample using a mass spectrometer.

According to one aspect of the present invention, there is provided a method for detecting and measuring the degree of phosphorylation in a sample, comprising: (i) introducing the sample containing an analyte into an inductively coupled plasma mass spectrometer having a reactive collision cell, and producing analyte ions, (ii) reacting the analyte ions with a reactive gas, producing product ions with a different mass to charge ratio than the analyte ions which provides interference-free detection, (iii) detecting and measuring a signal or combination of signals from a product phosphorus-containing ion and a signal or combination of signals from a second ion, wherein the second ion is specific to the sample and is one of an ion and a plurality of ions, and (iv) computing one of the ratio and plurality of ratios, of the signal or combination of signals from the product phosphorus-containing ions to the signal or combination of signals from the second ions, to determine the degree of phosphorylation in the sample.

According to another aspect of the present invention, there is provided a system that detects and measures the degree of phosphorylation in a sample, comprising: (i) means for introducing the sample containing an analyte into an inductively coupled plasma mass spectrometer having a reactive collision cell, and producing analyte ions, (ii) means for reacting the analyte ions with a reactive gas, producing product ions with a different mass to charge ratio than the analyte ions which provides interference-free detection, (iii) means for detecting and measuring a signal or combination of signals from a product phosphorus-containing ion and a signal or combination of signals from a second ion, wherein the second ion is specific to the sample and is one of an ion and a plurality of ions, and (iv) means for computing one of the ratio and plurality of ratios, of the signal or combination of signals from the product phosphorus-containing ions to the signal or combination of signals from the second ions, to determine the degree of phosphorylation in the sample.

According to another aspect of the present invention, there is provided the use of an inductively coupled mass spectrometer having a reactive collision cell for the detection and measurement of the degree of phosphorylation in a sample.

Other features and advantages of the present invention will become apparent from the following detailed description. It should be understood, however, that the detailed description and the specific preferred embodiments of the invention are given by way of illustration only, since various changes and modifications within the spirit and scope of the invention will become apparent to those skilled in the art from this detailed description.

BRIEF DESCRIPTION OF THE FIGURES

The invention will now be described in relation to the figures, in which.

DETAILED DESCRIPTION OF THE INVENTION

Definitions

Figure 1:
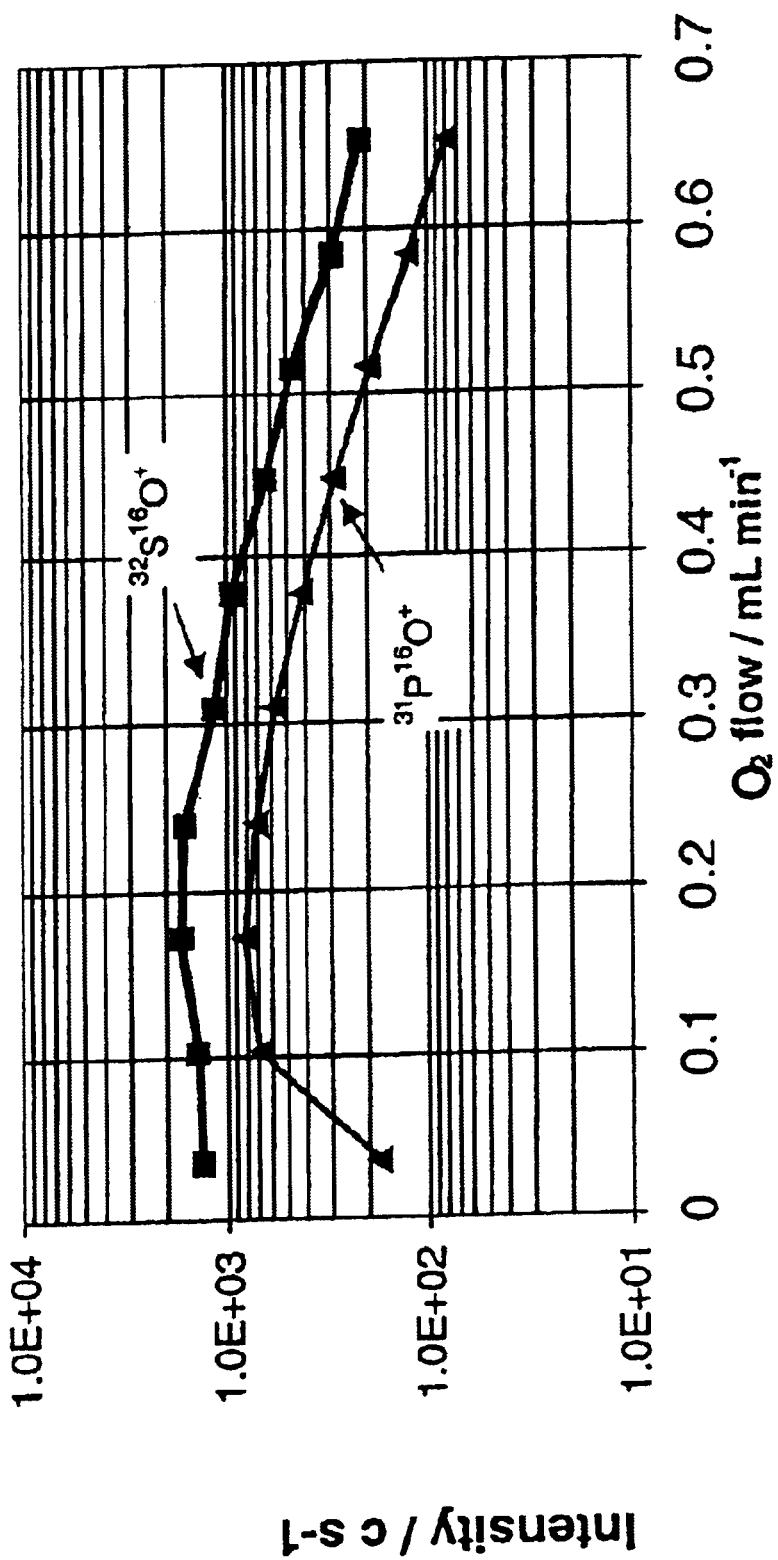
FIG. 1 is a graph showing the formation and detection of $PO^+$ and $SO^+$ from a sample of 10 ppb P and S in deionized water, wherein the analyte ions, $P^+$ and $S^+$, reacted with the reactive gas, $O_2$. Net signals (blank subtracted) for $PO^+$ and $SO^+$ for $P^+$ and $S^+$ reaction with $O_2$. Neb=1.05, q=0.4 a=0.02, Clean Lab DRC.

As used in this application,

"analyte" means any substance being identified and measured in an analysis, and includes but is not limited to: proteins, polypeptides, cells, cell lysates, cell lines, nucleic acids and sugars and mixtures thereof.

"analyte ions" means ions formed in the inductively coupled plasma when the sample is introduced in the ICP-MS, wherein the sample is completely disintegrated, atomized and ionized so that ions (usually atomic and usually singly charged) are formed. In this application, the analyte ions are the ions originating in the ICP and are differentiated from the product ions that are formed in the reactive collision cell.

"biologically active material" means any biological substance found in nature and includes but is not limited to: antibodies, antigens, proteins, ligands, receptors, cells, viruses and nucleic acids.

"inductively coupled plasma" (ICP) means a source of atomization and ionization in which a plasma is established in an inert gas (usually argon) by the inductive coupling of radiofrequency energy. The frequency of excitation force is in the MHz range.

"isobar" means an ion having the same mass to charge ratio as another ion.

"isobaric interference" occurs when isobars obscure or interfere with analyte ions, such that one can not differentiate between ions. Such interferences are common in mass spectrometry.

"interference-free detection" means detection without isobaric interference.

"mass spectrometer" means an instrument for producing ions and analyzing them according to their mass to charge ratio.

"product ions" means the ions produced in the reactive collision cell after reaction with the reactive gas with the analyte ions. Product ions have a different mass to charge ratio than analyte ions.

"reactive collision cell" means a cell wherein analyte ions react with a gas forming product ions with a different mass to charge ratio than the analyte ions.

"reactive gas" means a gas or combination of gases that are used in the reactive collision cell to form product ions or to remove interfering ions and thus resolve isobaric interference.

"sample" means any composition of liquid, solid or gas containing or suspected of containing an analyte.

"second ion" means an any ion or ions other than phosphorus-containing ions that are representative of (i.e. specific to) the sample. The second ion can be analyte ions, product ions, or combinations of both.

The invention relates to a method for detecting and measuring the degree of phosphorylation in a sample by introducing the sample into an inductively coupled plasma mass spectrometer which is connected to a reactive collision cell. In the reactive collision cell, the analyte ions are converted into product ions by reactions with a reactive gas, distinguishing themselves from interfering ions, thus minimizing isobaric interference. The degree of phosphorylation is calculated by the ratio of phosphorus-containing ion to second ion, the second ion being specific to the sample.

Any sample may be used. Preferably, the sample is a biological sample. Preferably the sample comprises protein, polypeptide, cell, cell lysates, cell lines, nucleic acids, sugars, or mixtures thereof. Optionally, the sample contains SDS denatured proteins.

The sample is introduced into an inductively coupled plasma mass spectrometer having a reactive collision cell. Techniques using ICP-MS can be applied for the purposes of this invention, such as those described by Tanner et al. (2000), Baranov et al. (1999), Tanner and Baranov (1999), Tanner and Baranov (2000), and Bandura et al. (2000). This successful modification of ICP-MS includes the dynamic reaction cell, which is used in order to reduce isobaric interferences in atomic mass spectrometry. Briefly, the ICP-DRC-MS technique comprises a high temperature plasma in which the sample particles are atomized and ionized, a vacuum interface which is designed to transport the plasma together with analyte ions from atmospheric pressure to vacuum, an ion focusing optics, and the dynamic reaction cell for chemical modification of the ion current and mass analyzing device (quadrupole, TOF or magnetic sector).

A low resolution ICP-MS may be used, which is inexpensive compared to a high resolution ICP-MS. The current state-of-art uses 'high resolution' ICP-MS for the detecting and measuring the degree of phosphorylation in samples (Wind et al., 2001) because high resolution ICP-MS is needed for detecting $P^+$ and $S^+$ in order to overcome isobaric interferences. The present invention overcomes the need to use high resolution ICP-MS, by the addition of the reactive collision cell, which reacts the $P^+$ and $S^+$ ions to form their product ions at a different mass to charge ratio, avoiding isobaric interference.

Preferably, the reactive collision cell is a Dynamic Reaction Cell™. In a preferred embodiment, the pressure and other parameters of the reactive collision cell are controlled to minimize fluctuations of the ion flux density.

The sample may be introduced to the ICP-MS by known means, and is usually introduced to the plasma as a spray of droplets (liquid sample) or flow of particles (laser ablation of solid surfaces).

The sample containing analyte ions is reacted with a reactive gas, producing product ions with a different mass to charge ratio than the analyte ions, which provides interference free detection. The choice of reactive gas is made on the ability of the reactive cell to convert sample (analyte) ions to product ions with a different mass to charge ratio. The following gases are good candidates: $O_2$, $N_2O$, $CO_2$, $CH_3F$, $CH_4$, $C_2H_4$ and $C_2H_6$.

Signals or combinations of signals from a product phosphorus-containing ion and signals and combinations of signals from a second ion in the sample are detected and measured, wherein the second ion is specific to the sample. By combination of signals is meant a sum of different product ions of the same analyte ion, for example, $PO^+$ and $POH^+$, or $PO^+$ and $PF^+$ (if the mixture of $O_2$ and $CH_3F$ is used as a reactive gas). Another example of a combination of signals is a sum of analyte and/or product ions of more than one analyte ion, for example, $SO^+$, $Na^+$ and $^{13}C^+$ signals can be combined to characterise the amount of the protein sample, while $PO^+$ signal characterises the degree of phosphorylation. The signals can be from a combination of product ions and original "analyte" ions. The choice of the elements in the second ions to measure is made on the basis of selectivity for the sample and ability to detect and measure it accurately. For protein samples, sulfur is the logical choice, as the ions of hydrogen, nitrogen, oxygen and carbon are highly abundant in an ICP-MS background spectra and as those elements are always present in the solvents and reagents used to prepare the samples. Sulfur is present in proteins in methionine and cysteine residues, and in disulphide bonds. Optionally, the product ions contain fluorine atom(s) or an alkyl group. Optionally, the product ions can be the products of condensation, addition, nucleophilic substitution or atom (group) subtraction reactions. The second ion can be a non-phosphorus containing analyte ion, a non-phosphorus containing product ion or a combination of both. Preferably, the second ion is a product sulfur-containing ion or an analyte sodium ion. Optionally, the product ions are ions that have been oxidized.

The ratio of product phosphorus ion to second ion is computed in order to determine the degree of phosphorylation. For example, milk protein α s2 casein is known to have 10 phosphates, 2 cysteines and 4 methionines. The measured ratio of $PO^+/SO^+$ should be (after instrument response factors are accounted for) 10:6. De-phosphorylated α s2 casein should yield a lower $PO^+/SO^+$ ratio. The activity of de-phosphorylating reagents thus can be assessed by comparing the measured $PO^+/SO^+$ for natural and reacted protein samples.

In another embodiment, a plurality of product ions are measured, including product phosphorus ion, such that multiple ratios of phosphorus to product ion are computed. This is advantageous in that results can be confirmed. Additionally, a plurality of isotopes of product phosphorus ions and other product ions can be measured to confirm results.

In another embodiment, the gas pressure and other parameters of the reactive collision cell are set to the values that provide sufficient reduction of ion flux density fluctuations and temporal homogenization of the ion flux, in a manner similar to that described in Bandura et al., 2000. Reduced fluctuations and the temporal homogenization provide improved precision of the ion intensity ratio measurements.

In another embodiment, the reactive collision cell incorporates an accelerating axial field that allows efficient transport of the product ions towards the exit of the cell and helps to overcome scattering losses in cases when a relatively heavy reaction gas is used.

In yet another embodiment, the axial field in the reactive collision cell is decelerating, which allows more efficient temporal homogenization and ion flux density fluctuation reduction when a relatively light reaction gas is used.

In another embodiment, the sample contains SDS denatured proteins and the second ion is $Na^+$.

Optionally, a biologically active material is tagged with an element, such that the biological active material binds with the analyte in the sample. In this way, the tagging element is representative of the sample, and acts as the second ion. For example, an antibody which binds specifically to the antigen of interest, is tagged with the element, then the antibody-antigen complex is introduced into an ICP-MS, and the ions containing the tagging element are used as second ions, while product phosphorus-containing ions are used to detect the amount of phosphorus.

Optionally, the analyte is tagged directly with an element, wherein the second ion contains a tagging element.

The advantages of this method are many. First, the accuracy and simplicity of the method renders it usable for proteomics, where numerous proteins samples are tested in high throughput screenings. Second, the system allows for the simultaneous determination of phosphorus concentration and sample concentration. This produces very accurate results in a very short time. Third, confirmation of the results is possible, by using other product ions or other isotopes as comparisons. Fourth, the use of the reactive collision cell allows for 'chemical resolution', which does not restrict the solvent load of the plasma, as is the case in 'high resolution' ICP-MS. Further chemical resolution shifts analyte ions 16 masses up (if oxidized) from the interference, thus a higher practical resolution is attained. Fifth, laser ablation can be employed as a means of introducing samples into the low resolution ICP-MS, as chemical resolution is not affected by the variable content in the ablated sample of N, O, H and C, the elements that form isobaric interferences for $P^+$ and $S^+$, as the latter are measured at a different mass-to-charge ratio as product ions. This is in contrast to "high resolution" ICP-MS which measures ions at their native mass-to-charge ratio, the background at which is defined by the abundance of interference-forming elements (N,O,H,C) in the sample and can vary significantly during the ablation. The variability of the background during the ablation can be caused, for example, by high porosity and variable polymer density of the polyacrylamide gel used for electrophoretic separation of proteins. Finally, the low resolution ICP-MS is more compact, less expensive and generally is more suited for routine use compared to the high resolution ICP-MS.

The invention is set forth with the following examples. The examples are non-limiting and are merely representative of various aspects and features of the present invention. Example 1 illustrates how a reactive collision cell minimizes isobaric interference. Example 2, 3, 4, 5, 6, 7 and 8 demonstrate how the degree of phosphorylation in a sample is determined by this method.

EXAMPLE 1

Experimentation Using $O_2$ as a Reactive Gas in the Reactive Collision Cell

The use of $O_2$ as a reactive gas for oxidation, is an efficient means for the simultaneous resolution of $P^+$ and $S^+$ from the polyatomic interferences. Product ions of $PO^+$ and $SO^+$ were detected. Relevant reaction enthalpy change $\Delta H_r$ was calculated using thermochemistry data (Lias et al, 1988), and most of the thermal rate constants have been reported (Anicich 1993) and summarized in the Table I below.

TABLE 1

Reaction data for $P^+$ and $S^+$ and relevant interfering ions

| # | 1. Reaction | Reaction enthalpy change $\Delta H_r$/kcal/mole | Thermal reaction rate constant $k_r$/molecule$^{-1}$ cm$^3$ s$^{-1}$ |
|---|---|---|---|
| 1 | $P^+ + O_2 = PO^+ + O$ | −71.4 | $4.9 \times 10^{-10}$ |
| 2 | $S^+ + O_2 = SO^+ + O$ | −6.2 | $2.3 \times 10^{-11}$ |
| 3 | $CO^+ + O_2 = CO_2^+ + O$ | −13.5 | $<2 \times 10^{-14}$ (no reaction) |
| 4 | $HCO^+ + O_2 = COOH^+ + O$ | 3.3 | $<2 \times 10^{-13}$ (no reaction) |
| 5 | $NO^+ + O_2 = NO_2^+ + O$ | 57.4 | $<1 \times 10^{-11}$ (no reaction) |
| 6 | $NOH^+ + O_2 = NO_2^+ + O$ | 19.3 | No data |
| 7 | $O_2^+ + O_2 = O_3^+ + O$ | 102.1 | No data |
| 8 | $Ti^+ + O_2 = TiO^+ + O$ | −46.1 | $5.0 \times 10^{-10}$ |

Reactions for $P^+$ and $S^+$ were both exothermic, with $P^+$ reacting much faster than $S^+$ under thermal conditions. Reactions for $HCO^+$, $NO^+$, $NOH^+$, $O_2^+$ were endothermic and could not proceed under standard thermal conditions. The only exothermic reaction of $CO^+$ was reaction #3 and it was reported as not proceeding. Reference data for $Ti^+$ is provided, as it can potentially interfere with $PO^+$ and $SO^+$. $Ti^+$ is shifted to its oxide by the same oxidation reaction at approximately the same rate as $PO^+$ formation. Thus, the method is tolerant to the presence of some $Ti^+$ in the sample. Normally, one would not expect much Ti in biological samples, however, care should be taken to ensure that the buffers and reagents used in sample preparation do not contain it.

Figure 2:
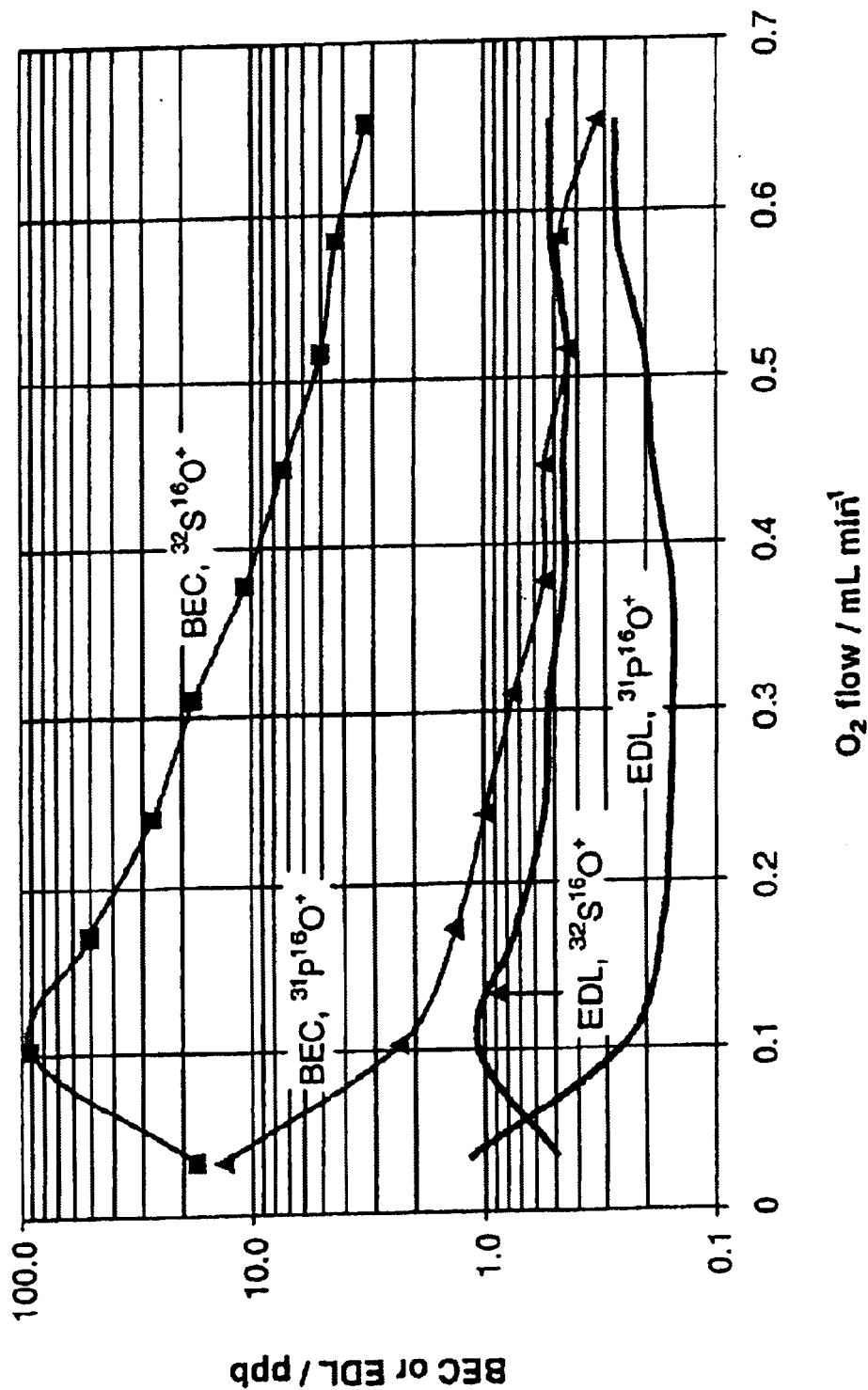
FIG. 2 is a graph showing the calculated background equivalent concentration (BEC) and 5 second integration estimated detection limit (EDL) for the data of FIG. 1. $PO^+$ and $SO^+$ background equivalent concentrations (BEC) and limits for detection (estimated for 5 s integration) as a function of $O_2$ flow. Neb=1.05 q=0.4 a=0.02, Clean Lab DRC.

FIG. 1 shows a typical example of the implementation of reactions (1) and (2) to oxidize $P^+$ and $S^+$ in the ICP-DRC™-MS. Operating at $O_2$ flow of about 0.2 mL/min gave maximum signals for $PO^+$ and $SO^+$, however background equivalent concentrations (BEC) and estimated 1-s detection limits were better at higher flow, as is demonstrated in FIG. 2. In practice, BEC of 0.53 and 4.8 ppb and 5-second detection limits (3σ) of 0.2 and 0.52 ppb were measured at a compromise $O_2$ flow of 0.52 mL/min (this corresponds to 0.75 arb.un. setting of the mass flow controller used in the instrument). Experimental parameters that were used when obtaining data presented here, are given in the Table 2.

TABLE 2

Parameters of the ICP-DRC ™-MS during the measurements

| | |
|---|---|
| Nebulizer Gas Flow [NEB] | 1.01 L/min |
| Auxiliary Gas Flow | 1 L/min |
| Plasma Gas Flow | 15 L/min |
| Lens Voltage | 5.1 V |
| ICP RF Power | 1100 W |
| Analog Stage Voltage | −1887.5 V |
| Pulse Stage Voltage | 1300 V |
| Quadrupole Rod Offset Std [QRO] | 0 V |
| Cell Rod Offset Std [CRO] | −16 V |
| Discriminator Threshold | 65 mV |
| Cell Path Voltage Std [CPV] | −17 V |
| RPa | 0.02 |
| RPq | 0.4 |
| DRC Mode NEB | 1.05 L/min |
| DRC Mode QRO | −6.5 V |
| DRC Mode CRO | −1 V |
| DRC Mode CPV | −17 V |
| Cell Gas A | 0 |
| Cell Gas B | 0.75 arb.un |
| RF Voltage | 200 V |
| DC Voltage | 0 V |

EXAMPLE 2

Detection and Measurement of Phosphorus and Sulfur in Spiked Deionized Water

Figure 3:
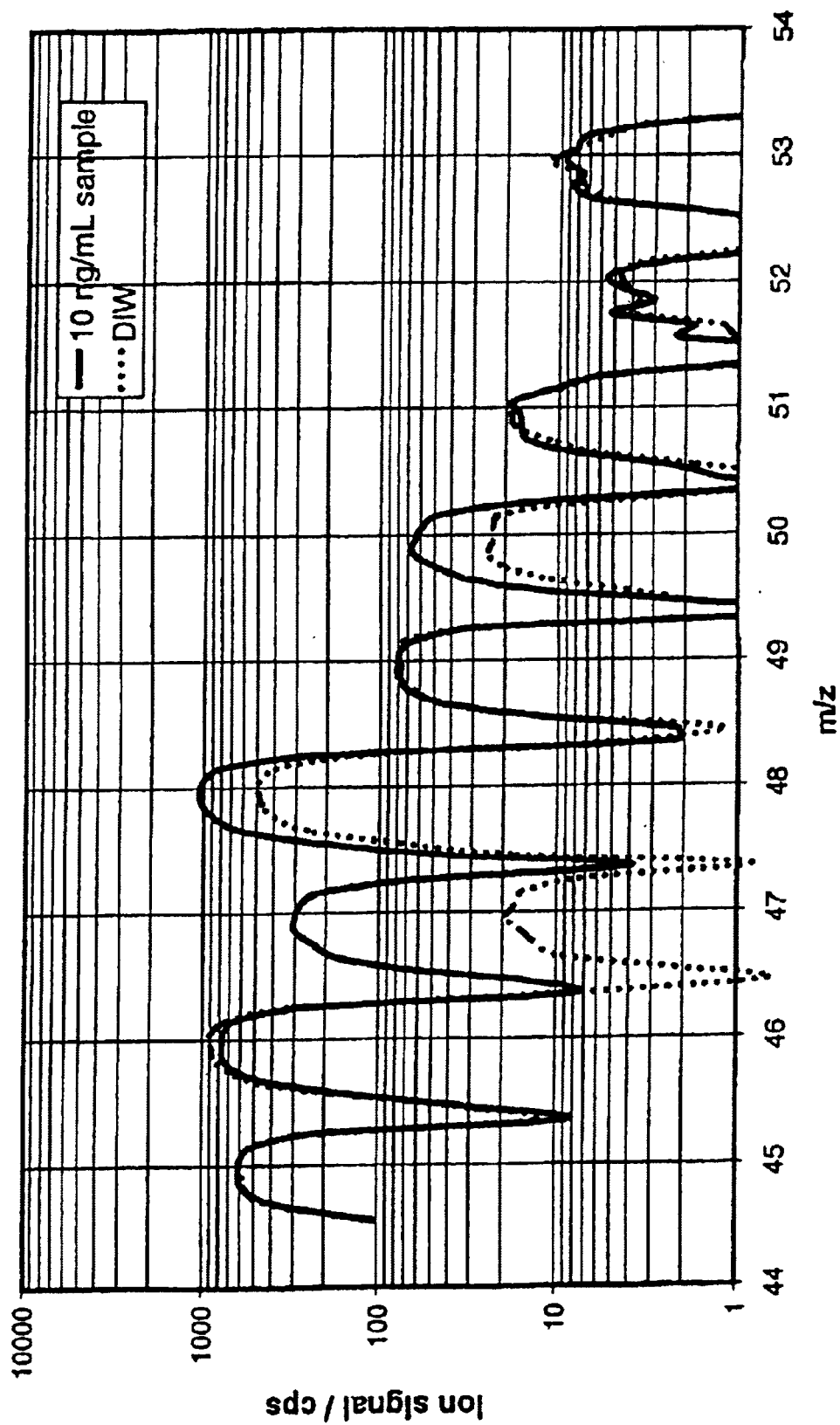
FIG. 3 shows a mass spectra comparing blank (deionized water) and sample (10 ppb P and S in deionized water) analysis using an ICP-DRC™-MS under the conditions listed in Table 2, using $O_2$ as the reactive gas.

Typical mass spectra of a sample containing 10 ppb of P and S in deionised water (DIW) and of the DIW collected under these conditions are shown in FIG. 3. The relatively high background and detection limit for $^{32}S^{16}O^+$ is likely to be limited by the presence of sulfur in the blank, as the measured ratio $^{34}S^{16}O^+/^{32}S^{16}O^+=0.0477$ is close to the natural abundance ratio (0.0443).

Figure 4:
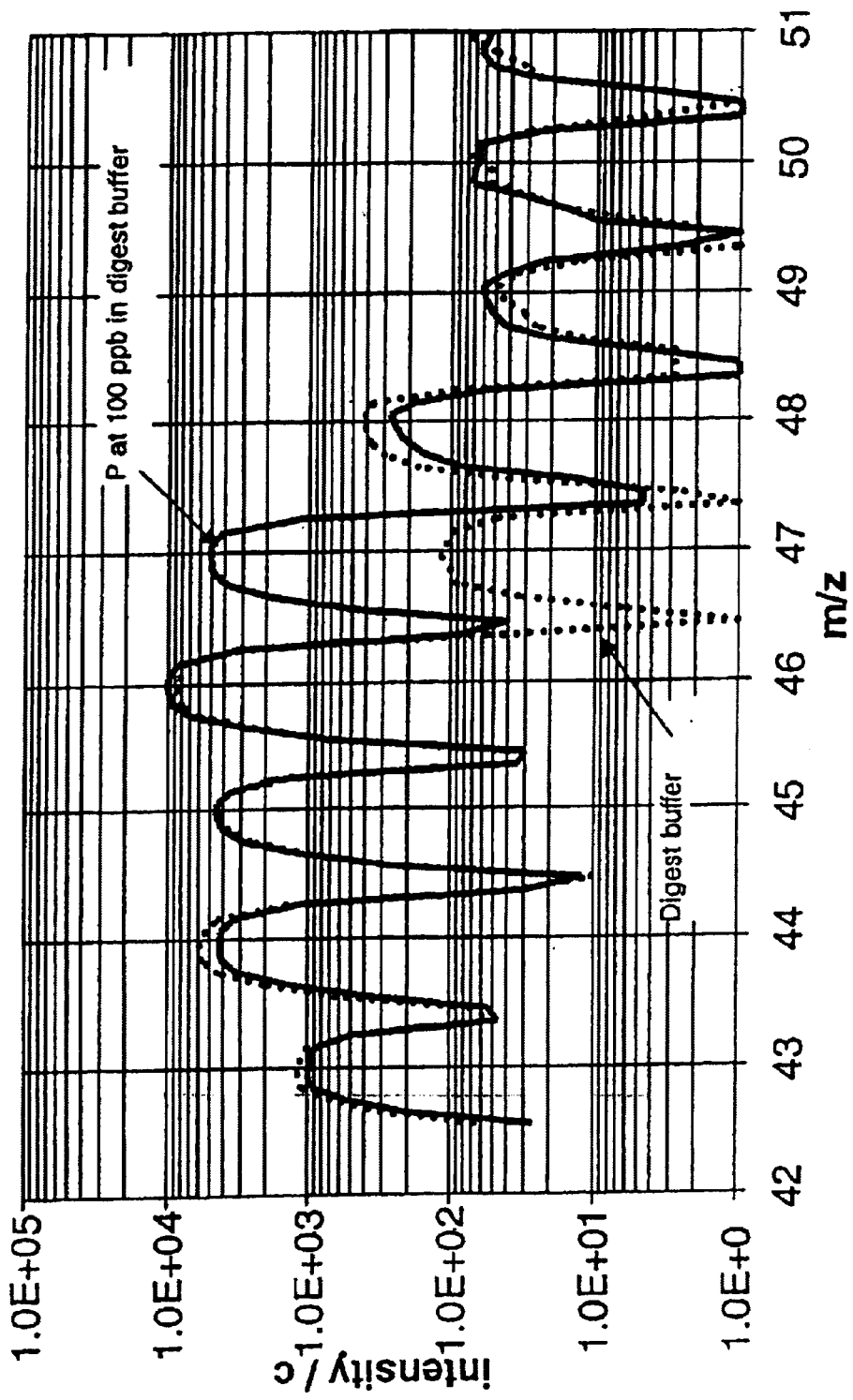
FIG. 4 shows a mass spectra of a sample containing 100 ppb P in the digest buffer containing 5% $CH_3CN$+5% $CH_2O_2$ and 1 mM of $NH_4HCO_3$ in deionized water and a digest blank. The reactive gas used was $O_2$ at a flow rate of 0.75 arb.un. Nebulizer gas flow of 0.8 L/min was used to ensure robustness of plasma and full decomposition of highly concentrated organic matrix.

Thus, the method allows chemical resolution of $P^+$ and $S^+$ from typical ICP MS interferences and detection at the level of sub-ppb (picogram/microliter) while using low-resolution ICP-MS. Moreover, the detection capability is relatively independent of the sample content. An example of the mass spectrum for the sample containing 100 ppb of P in a digest buffer containing 5% $CH_3CN$+5% $CH_2O_2$ and 1 mM of $NH_4HCO3$ as shown in FIG. 4 demonstrates that BEC of about 2 ppb for P is achievable for such a high content of interfering elements.

EXAMPLE 3

Determination of the Degree of Phosphorylation in Purified β-casein

Figure 5:
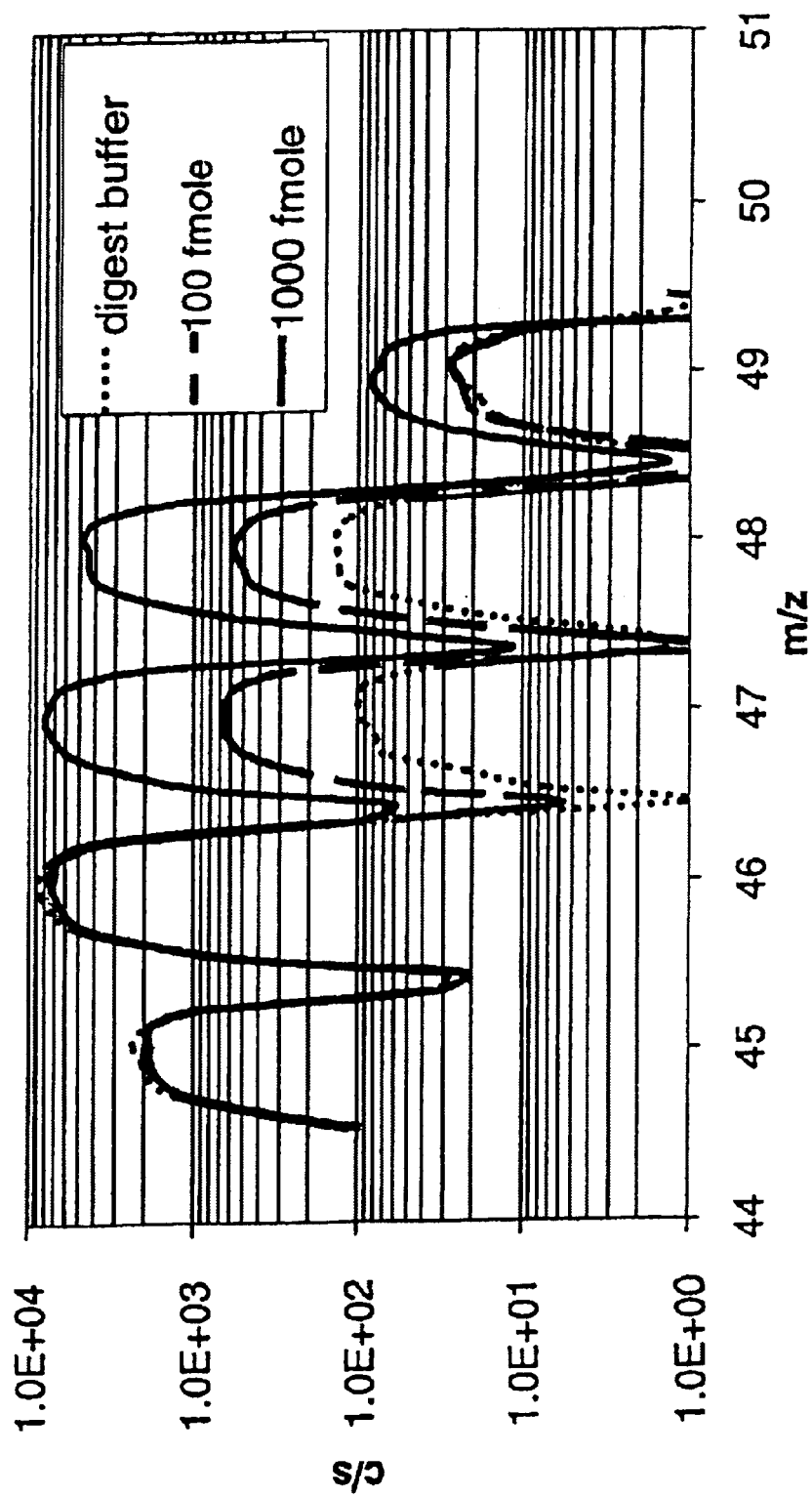
FIG. 5 shows a mass spectra of various concentrations of β-casein in digest buffer (5% $CH_3CN$+5% $CH_2O_2$ and 1 mM of $NH_4HCO_3$ in deionized water), as determined using $O_2$ as reactive gas at 0.75 arb.un.
Figure 6:
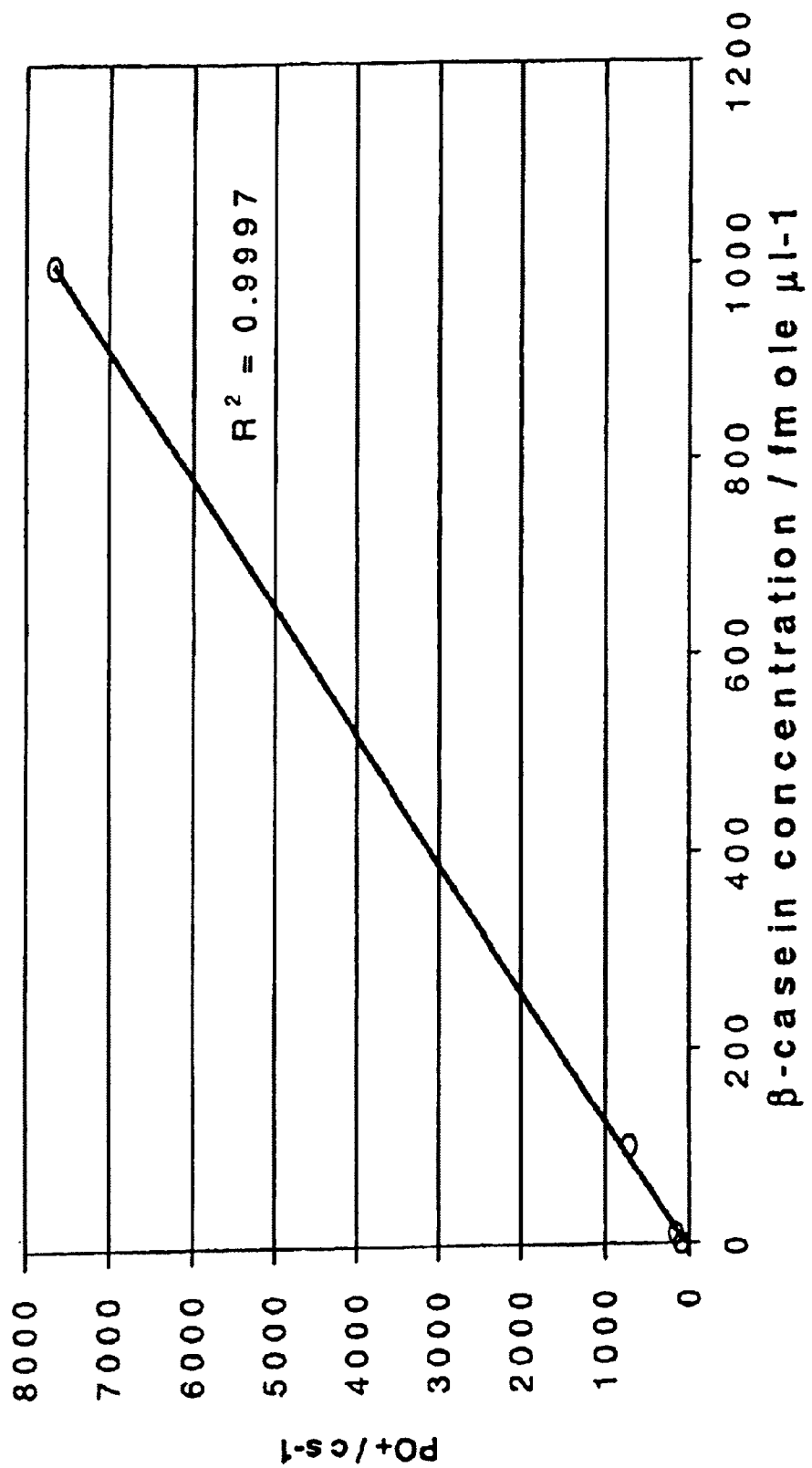
FIG. 6 is a calibration curve for $PO^+$ response versus β-casein concentration measured at 0, 10, 100, 1000 fmole/uL.

A low resolution ICP-MS was used to determine the degree of phosphorylation of the purified protein β-casein. The reactive gas was $O_2$. FIG. 5 shows mass spectra for samples containing 0, 100 and 1000 femtomole/microliter of β-casein in digest buffer of the same composition as described above. The response for $PO^+$ was linear in the range of β-casein concentrations from 0 to 1000 femtomole/microliter (see FIG. 6). The ratio $PO^+/SO^+$ in the studied protein concentration range varied from 1.18 to 1.29.

EXAMPLE 4

Determination of the Degree of Protein Phosphorylation in Human Embryonic Kidney 293 cell line (HEK 293)

Initial studies also showed that the ratio of P/S measured as $PO^+/SO^+$ by the ICP-DRC™-MS in accordance with the developed method, can indicate the state of phosphorylation for the unpurified mixture of the cell proteins contained in cell lysates, showing good correlation of the ratio for similar cell cultures even for significantly different total protein concentration, as well as showing difference in ratio for different cell cultures for similar absolute signals of P.

Table 3 shows the P/S ratios for the lysates of the HEK 293 cell line (Human Embryonic Kidney cells) prepared in different buffers and measured over the course of several days with different sample dilution factors, using 2 different instruments under similar operating conditions. Cells were prepared (Day 1) and were collected from dishes in TBS (Tris buffered saline) and homogenized using reduced KLB lysis buffer (containing Tris, NaCl and NP-40). Each sample contained (before dilution) approximately $10^7$ cells.

Cells prepared on 3 other days (Day 2, 3, and 4), were washed in dishes in TBS, then buffer was dried and concentrated HCL added, after which the lysate was scraped off into sample tubes.

TABLE 3

Results for repeated preparation and measurements of P and S content for HEK293 cell lysates.

| | PO+ | 32SO+ | 34SO+ | PO+/SO+ | 34SO+/32SO+ |
|---|---|---|---|---|---|
| Day 1, reduced KLB lysis buffer, 1:100 dilution with DIW, DRC #1 (clean lab) | | | | | |
| HEK293-1 | 23555 | 15659 | 947 | 1.504 | 0.060 |
| HEK293-2 | 23914 | 15861 | 979 | 1.508 | 0.062 |
| HEK293-3 | 22092 | 15297 | 899 | 1.444 | 0.059 |
| HEK293-4 | 22797 | 14936 | 915 | 1.526 | 0.061 |
| Day 2, concentrated HCL, 1:20 dilution with DIW, DRC #1 (clean lab) | | | | | |
| HEK293-1 | 157023 | 117181 | 6865 | 1.340 | 0.059 |
| HEK293-2 | 153103 | 113692 | 6691 | 1.347 | 0.059 |
| HEK293-3 | 157488 | 115882 | 6799 | 1.359 | 0.059 |
| HEK293-4 | 135977 | 102473 | 6032 | 1.327 | 0.059 |
| Day 3, concentrated HCl, 1:50 dilution with DIW, DRC #2, research lab | | | | | |
| HEK293-1 | 78127 | 66756 | 3710 | 1.170 | 0.056 |
| HEK293-2 | 87685 | 73855 | 4041 | 1.187 | 0.055 |
| HEK293-3 | 71833 | 59602 | 3258 | 1.205 | 0.055 |
| Day 4, concentrated HCl, 1:10 dilution with DIW, DRC #2 (research lab) | | | | | |
| HEK293-1 | 518003.6 | 416451 | 22738 | 1.244 | 0.055 |
| HEK293-2 | 421511.4 | 366104 | 19923 | 1.151 | 0.054 |
| HEK293-3 | 488301.1 | 424429 | 23074 | 1.150 | 0.054 |
| HEK293-4 | 517139.2 | 431385 | 23334 | 1.199 | 0.054 |
| HEK293-5 | 535357.8 | 445222 | 24172 | 1.202 | 0.054 |
| HEK293-6 | 492968.4 | 432567 | 23571 | 1.140 | 0.054 |
| Average | 229816 | 189844 | 10468 | 1.294 | 0.057 |
| RSD, % | 91 | 94 | 92 | 10.508 | 4.832 |

Despite significant variation in absolute signals for $^{31}PO^+$ and $^{32}SO^+$ (about 90% RSD) measured for 17 different cell lysate samples incubated and prepared in 4 different groups of cell cultures on 4 different days, variation of the ratio of $PO^+/SO^+$ was much smaller (10.5% RSD). Detection of a second S isotope ($^{34}SO^+$) gave additional verification of the absence of interferences during S measurement, thus providing additional "quality control".

The method can be quantitative in distinguishing the state of phosphorylation of different samples, even if the amounts of the compared samples differ significantly, provided the samples have similar concentrations of sulfur-containing amino-acid residues (i.e. cysteine and methionine).

EXAMPLE 5

Detecting and Measuring Protein Phosphorylation from Samples Electrophoresced on a Polyacrylamide Gel and Introduced into the ICP-MS by Laser Ablation A protein mixture is separated electrophoretically on a polyacrylamide gel. The polyacrylamide matrix is ablated (dry particles) into the ICP to be atomized and ionized for MS. A variation of this example, uses a denaturing gel, where the proteins are boiled in a buffer containing β-mercaptoethanol and sodium dodecyl sulfate (SDS), so that the disulphide bridges that hold together the tertiary protein structure, are reduced and the SDS molecules bind to the protein. Each protein becomes a rod-shaped structure with a series of SDS molecules along the polypeptide chain. Thus, the denaturing process is also a 'tagging' process—and S and Na that are present in SDS ($CH_3(CH_2)_{10}CH_2OSO_3Na$) are used to characterize total protein. The degree of protein phosphorylation is determined by measuring P as $PO^+$, S as $SO^+$ and Na as $Na^+$ (Na does not react with most reactive gases).

EXAMPLE 6

Determining the Degree of Phosphorylation of an Antigen Bound to an Element-tagged Antibody A protein mixture is reacted with an antibody which is tagged with an element (for example, Eu) or nanoparticle (for example, Nanogold™), as described in U.S. Provisional Patent application #60/258,387 entitled, "Elemental analysis of tagged biologically active materials". The antigen-antibody complex is separated from the mixture. Analyte ions that contain the tag element (Eu or Au in our examples) and analyte ions of phosphorus are reacted with, for example, $O_2$. Product ions $PO^+$ are measured interference-free for determining the amount of phosphorus, while product ions $EuO^+$ or analyte ions $Au^+$ are used as second ions to characterize the amount of the protein. Ratio of signals of $PO^+/EuO^+$ or $PO^+/Au^+$ characterises the degree of phosphorylation of the protein, provided the antibody contains known (if any) amount of phosphorus.

EXAMPLE 7

Figure 7:
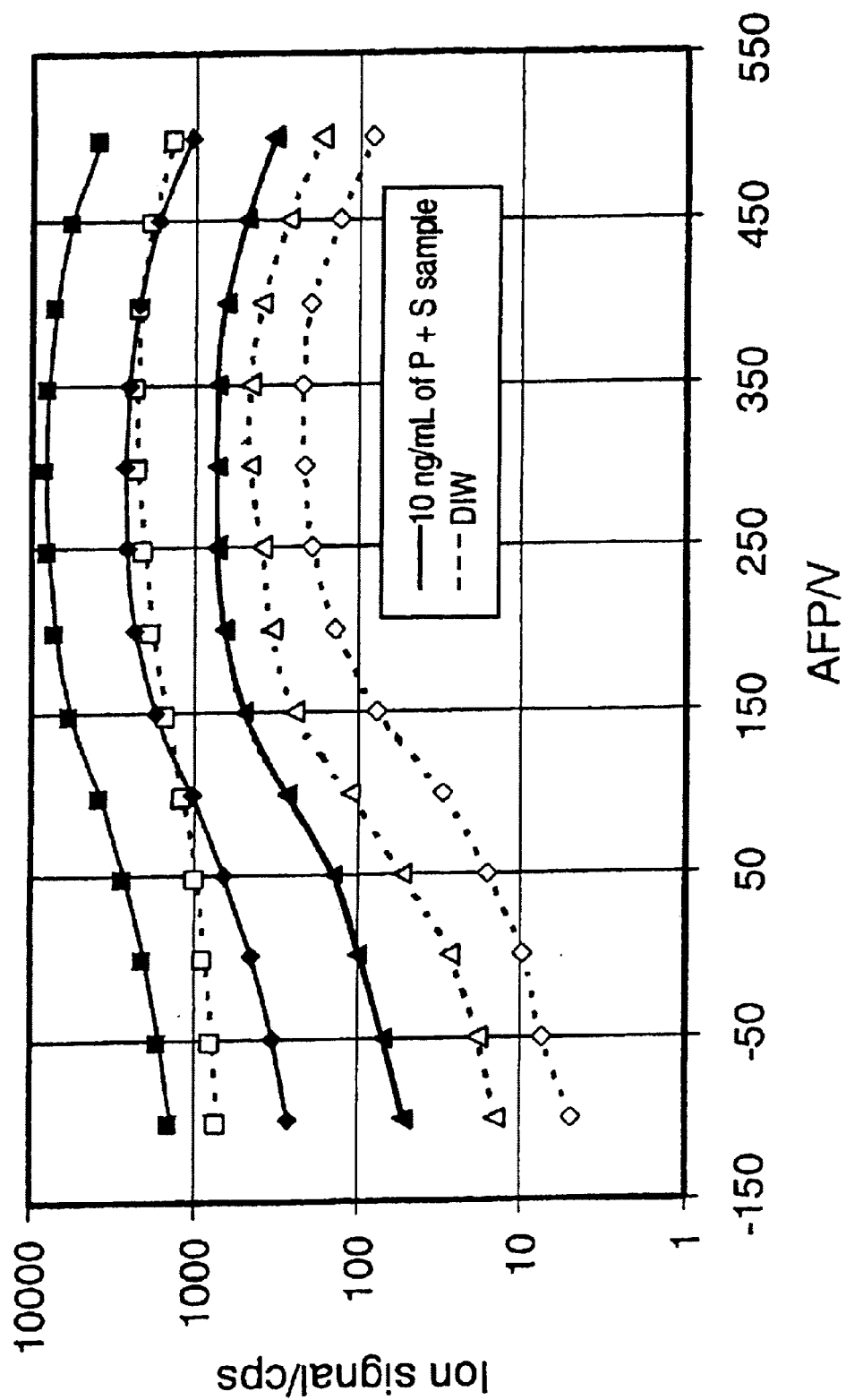
FIG. 7 is a graph that shows signals for $PO^+$ and $SO^+$ vs. Axial Field Potential (AFP) at $O_2$=0.5 arb.un., RPq=0.4, RPa=0.02 and nebulizer flow of 200 µL/min. Solid markers and lines –10 ng/mL of P and S sample, open markers and dotted lines-blank (DIW). Diamonds-m/z=47, squares-m/z=48, triangles-m/z=50.

Overcoming Scattering Losses in Cases when a Relatively Heavy Reaction Gas is Used In an effort to overcome scattering losses when a relatively heavy reaction gas is used, an accelerating axial field was introduced in the reactive collision to allow efficient transport of the product ions towards the exit of the cell. FIG. 7 graphs the signals for $PO^+$ and $SO^+$ versus axial field potential.

EXAMPLE 8

Figure 8:
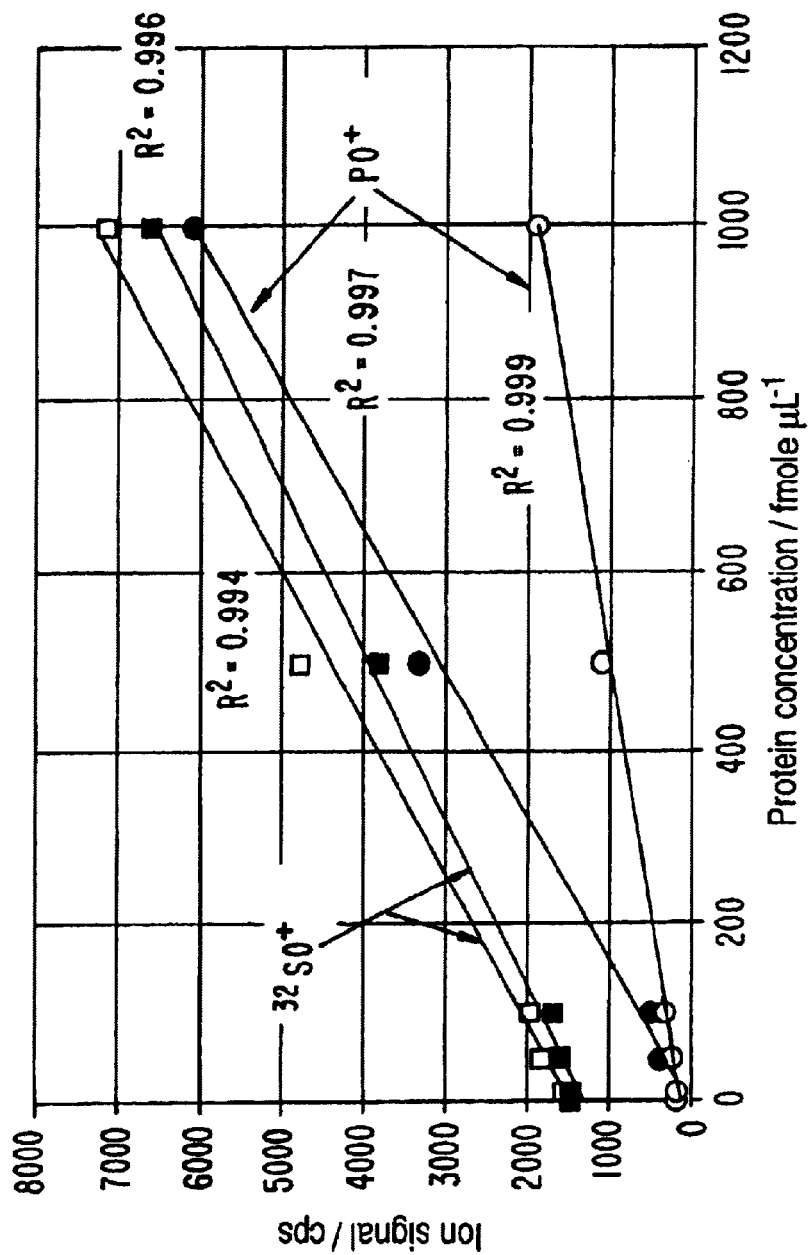
FIG. 8 is a graph that shows the calibration curve for $PO^+$ and $^{32}SO^+$ response versus protein concentration for regular and de-phosphorylated α-casein. Calibration for regular (solid markers) and de-phosphorylated (open markers) α-casein. $O_2$=0.5; RPq=0.4; RPa=0.02; micronebulizer at 16 µL/min. Circles-$PO^+$, squares-$^{32}SO^+$.

Method of Quantitation of the Degree of Phosphorylation for Regular and De-phosphorylated α-casein The degree of phosphorylation of regular and de-phosphorylated α-casein was measured. A calibration curve for $PO^+$ and $^{32}SO^+$ response versus protein concentration for regular and de-phosphorylated a-casein is shown in FIG. 8.

The invention is intended to cover various modifications and equivalent arrangements included within the spirit and scope of the appended claims.

All publications, patents, and patent applications are herein incorporated by reference in their entirety to the same extent as if each individual publication, patent or patent application was specifically and individually indicated to be incorporated by reference in its entirety.

References

Anicich V. G. 1993. Ion reactions databases. The Astrophysical Journal Supplement Series, vol. 84 p. 215. Also, http://astrochem.jpl.nasa.gov/asch/

Bandura, D. R., Baranov, V. I., Tanner, S. D. 2000. Effect of collisional damping and reactions in a dynamic reaction cell on the precision of the isotope ratio measurements. J. Anal. At. Spectrom. 15: 921.

Baranov, V. I and Tanner, S. D. 1999 A dynamic reaction cell for inductively coupled plasma spectrometry (ICP-DRC-MS). Part I The rf-field energy contribution in thermodynamics of ion-molecule reactions. J. Anal. At. Spectrom. 14: 1133.

Baranov, V. I. and Tanner, S. D. 1999 A dynamic reaction cell for inductively coupled plasma mass spectrometry (ICP-DRC-MS). J. Anal At. Spectrom. 14: 1133–1142.

Baranov, V. I. and Tanner, S. D. 1998. Fundamental processes in an ICP-MS multipole reactive collision cell. Paper 1305, 1998 Pittsburg Conference on Analytical Chemistry and Applied Spectroscopy, New Orleans, La., March 4–9.

Bollinger, D. S. and Schleisman, A. J. 1999 Initial experience with the DRC ICP-MS, in Plasma Source Mass Spectrometry, Ed. G. Holland and S. D. Tanner p. 86.

Eiden, G. C., Barinaga, C. J., Koppenaal, D. W. 1997 Beneficial ion/molecule reactions in elemental mass spectrometry. Rapid Communications in Mass Spectrometry Vol. 11, 37–42.

Godovac-Zimmerman, J. and Brown, L. R. 2001. Perspectives for Mass Spectrometry and Functional Proteomics Mass Spectrometry Reviews 20: 1–57.

Houk, R. S., 1986 Analytical Chemistry 58: 97A–105A.

Lias, S. G., Bartmess, J. E., Liebman, J. F., Holmes, J. L., Levin, R. D., Mallard, W. G. 1988. Gas-phase ion and neutral thermochemistry. J. Phys. Chem. Ref. Data, Vol. 17 Suppl. 1

Tanner, S. D., Baranov, V. I, Vollkopf, U. 2000 A dynamic reaction cell for inductively coupled plasma mass spectrometry (ICP-DRC-MS). Part III. Optimization and analytical performance. J. Anal. At. Spectrom. 15: 1261.

Tanner, S. D. and Baranov, V. I. 2000 U.S. Pat. No. 6,140,638 Bandpass reactive collision cell.

Tanner, S. D. and Baranov, V. I. 1999. A dynamic reaction cell for inductively coupled plasma mass spectrometry (ICP-DRC-MS). Part II. Reduction of interferences produced within the cell. J. Anal. At. Spectrom. 10: 1083.

Tanner, S. D. and Baranov, V. I. 1999 Theory, Design, and Operation of a DRC for ICP-MS Atomic Spectrometry Vol 20 (2), March/April.

Tanner, S. D. and Baranov, V. I. 1998. Multidimensional interference rejection by Dynamic Reaction Cell ICP/MS. 25th Annual Conference of the Federation of Analytical Chemistry and Spectroscopy Societies, Austin, Tex., October 11–15.

Todd, J. F. J., Franklin, A. M., Smith, R. D. 2000 WO 01/01446 Method and apparatus for discriminating ions having the same nominal mass to charge ratio.

Wind, M., Wesch, H., Lehmann, W. D. 2001. Protein phosphorylation degree: Determination by capillary liquid chromatography and inductively coupled plasma mass spectrometry. Anal. Chem. paper AC10066S, published on Web, May 2001.

Wilson, K. and Walker, J. 2000 Principles and Techniques of Practical Biochemistry. Cambridge University Press pp 319–322.

We claim:

1. A method for detecting and measuring the degree of phosphorylation in a sample, comprising:
   (i) introducing the sample containing a phosphorylated analyte into a low resolution inductively coupled plasma mass spectrometer having a reactive collision cell, and producing analyte ions;
   (ii) reacting the analyte ions with a reactive gas, producing product ions with a different mass to charge ratio than the analyte ions which provides interference-free detection;
   (iii) detecting and measuring a signal or combination of signals from a product phosphorus-containing ion and a signal or combination of signals from a second ion, wherein the second ion is specific to the sample and is one of an ion and a plurality of ions; and
   (iv) computing one of the ratio and plurality of ratios, of the signal or combination of signals from the product phosphorus-containing ions to the signal or combination of signals from the second ions, to determine the degree of phosphorylation in the sample.

2. The method of claim 1 wherein the reactive collision cell is a Dynamic Reaction Cell™.

3. The method of claim 1 wherein the second ion or plurality of second ions are specific to the sample and are selected from the group consisting of non-phosphorus-containing analyte ions, non-phosphorus-containing product ions, and combinations thereof.

4. The method of claim 3 further comprising detecting and measuring a plurality of isotopes of the product phosphorus-containing ion and the second ions and computing a plurality of ratios of product phosphorus-containing ions to second ions.

5. The method of claim 3 wherein the second ion is selected from the group consisting of sulfur-containing ions and sodium.

6. The method of claim 3 wherein the sample is selected from the group consisting of proteins, polypeptides, cells, cell lines, cell lysates nucleic acids, sugars, and mixtures thereof.

7. The method of claim 3 wherein the product ions are ions that have been oxidized.

8. The method of claim 7 wherein the product ions have been oxidized by a reactive gas selected from the group consisting of $O_2$, $N_2O$ and $CO_2$.

9. The method of claim 3 wherein the product ions are ions that have been fluorinated.

10. The method of claim 9 wherein the fluorinated ions have been fluorinated by reactive gas $CH_3F$.

11. The method of claim 3 wherein the product ions contain an alkyl group.

12. The method of claim 11 wherein the alkyl group has been introduced by the reactive gas selected from the group consisting of $CH_4$, $C_2H_4$ and $C_2H_6$.

13. The method of claim 1 further comprising controlling the pressure and potentials on the field defining elements of the reactive collision cell.

14. The method of claim 1 further comprising controlling the axial field in the reactive collision cell such that it is accelerating.

15. The method of claim 1 further comprising controlling the axial field in the reactive collision cell such that it is decelerating.

16. The method of claim 1 wherein the step of sample introduction comprises laser ablation.

17. The method of claim 16 wherein the sample contains SDS denatured proteins and the second ion is $Na^+$.

* * * * *